(12) United States Patent
Kroll et al.

(10) Patent No.: US 6,625,493 B2
(45) Date of Patent: Sep. 23, 2003

(54) ORIENTATION OF PATIENT'S POSITION SENSOR USING EXTERNAL FIELD

(75) Inventors: Mark W. Kroll, Simi Valley, CA (US); Chris Sorensen, Valencia, CA (US); Gene A. Bornzin, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 55 days.

(21) Appl. No.: 09/939,197

(22) Filed: Aug. 24, 2001

(65) Prior Publication Data

US 2003/0040778 A1 Feb. 27, 2003

(51) Int. Cl.[7] ............................................. A61N 1/362
(52) U.S. Cl. ............................................. 607/17
(58) Field of Search ............................... 607/1–114

(56) References Cited

U.S. PATENT DOCUMENTS

| | | | |
|---|---|---|---|
| 5,425,750 A | 6/1995 | Moberg | 607/19 |
| 5,891,176 A | 4/1999 | Bornzin | 607/18 |
| 5,931,858 A | 8/1999 | Kadhiresan et al. | 607/20 |
| 5,941,904 A | 8/1999 | Johnston et al. | 607/19 |
| 5,957,957 A | 9/1999 | Sheldon | 607/17 |
| 6,002,963 A | 12/1999 | Mouchawar et al. | 607/18 |
| 6,044,297 A | 3/2000 | Sheldon et al. | 607/17 |
| 6,101,417 A * | 8/2000 | Vogel et al. | |
| 6,411,849 B1 * | 6/2002 | Shankar et al. | |
| 6,430,440 B1 * | 8/2002 | McNeil et al. | |
| 6,466,821 B1 | 10/2002 | Pianca et al. | 607/18 |

* cited by examiner

*Primary Examiner*—Scott M. Getzow

(57) ABSTRACT

An implantable cardiac stimulation device is equipped with an accelerometer-based sensor to sense a patient's movement and produce a vertical acceleration component indicative of a patient's acceleration in a vertical direction. A vertical velocity component is computed from the vertical acceleration component. The device may be further equipped with a magnetic field sensor to sense the earth's magnetic field as a way to obtain a true vertical orientation, against which the accelerometer-based sensor can be calibrated.

23 Claims, 7 Drawing Sheets

ORIENTATION OF PATIENT'S POSITION SENSOR USING EXTERNAL FIELD

RELATED APPLICATION

This patent is related to U.S. patent application Ser. No. 09,939,051, entitled "Detection of Patient's Position and Activity Status Using 3D Accelerometer-Based Position Sensor", which was filed concurrently herewith on Aug. 24, 2001, (Attorney Docket No. SJ1-001US).

TECHNICAL FIELD

The present invention generally relates to methods and systems for providing cardiac pacing therapy. More particularly, the invention concerns methods and implantable stimulation devices to detect a patient's position and activity status (e.g., going upstairs or downstairs, sitting or standing up from a supine position, etc.) using an accelerometer-based position sensor.

BACKGROUND

The cardiovascular system typically adjusts promptly and accurately to changes in a person's position and activity status. For instance, when a person walks or runs upstairs, the cardiovascular system increases the heart rate to compensate for the additional work being performed by the muscles. However, when a person walks downstairs, the cardiovascular system does not typically need to increase the heart rate (at least not nearly as much as when the person is going up the stairs). As another example, when an individual changes from a horizontal or supine position to a sitting or standing position, the cardiovascular system makes frequent and rapid adjustments to the heart rate and blood pressure to ensure sufficient blood flow to the brain.

When such adjustments are not accomplished, orthostatic hypotension can occur. Orthostasis means upright posture, and hypotension means low blood pressure. Thus, orthostatic hypotension describes the effects caused by low blood pressure when changing from a lying to an upright position, or perhaps from running upstairs. Orthostatic hypotension is defined as a decrease of at least 20 mm Hg in systolic blood pressure when an individual moves from the supine to upright position. The symptoms of orthostatic hypotension include dizziness, faintness, or lightheadedness that appear when standing. Other symptoms that often accompany orthostatic hypotension include chest pain, trouble holding urine, impotence, and dry skin from loss of sweating. Some patients with severe orthostatic hypotension are severely incapacitated.

For mobile and active patients with ineffective cardiovascular systems, cardiac stimulation devices are often used to provide pacing therapy that helps the cardiovascular systems meet the patents' demands. Unfortunately, conventional devices often cannot differentiate among various patient activities based simply on the patient's muscle activity. For instance, conventional cardiac stimulation may have difficulty discerning whether a patient is walking upstairs or downstairs, or is sitting or standing up following a prolonged period of rest in the supine position. The cardiac requirements for these various activities are significantly different and hence need to be accurately detected.

Ideally, the cardiac stimulation device would detect a patient's status. Such conditions might give rise to a situation where therapy is desired, such as treating for orthostatic hypotension with an increased pacing rate when the user stands up quickly.

Accordingly, there is a need for improved detection techniques for accurately detecting a patient's position and activity status so that appropriate pacing therapy can be selected and timely administered.

SUMMARY

An implantable cardiac stimulation device is programmed to administer pacing therapy in response to changes in a patient's position as detected by a 3D accelerometer-based position sensor. Such changes include climbing vertically upward or downward (e.g., walking upstairs/downstairs, rock/mountain climbing, etc.) and moving from a supine position to an upright position. Depending upon the position/activity change, a suitable pacing therapy (or omission of therapy) is applied, such as increasing the cardiac pacing rate when the patent walks upstairs, or sits up, to counteract any effects of orthostatic hypotension.

In the described implementation, the cardiac stimulation device is equipped with an accelerometer-based sensor to sense a patient's movement and produce a vertical acceleration component indicative of a patient's acceleration in a vertical direction. A vertical velocity component is then integrated from the vertical acceleration component. The device may be further equipped with a magnetic field sensor to sense the earth's magnetic field as a way to obtain a true vertical orientation, against which the accelerometer-based sensor can be calibrated. The device may further include a minute ventilation sensor to sense minute ventilation of the patient.

The cardiac stimulation device includes a processor coupled to the various sensors. The processor is programmed to determine a patient's position and activity status and whether to administer cardiac pacing therapy to the patient based on the vertical velocity and minute ventilation data. For instance, the processor might direct a pacing generator to increase a pacing rate in the event that the vertical velocity indicates an upward velocity and the minute ventilation shows an increase in breathing activity above a threshold.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

An implantable cardiac stimulation device is programmed to detect position and activity changes in a patient using acceleration and velocity components measured along a vertical axis, as well as minute ventilation. The stimulation device is equipped with a 3D accelerometer-based sensor to sense movements in the patient and to generate data representative of vertical acceleration. The device integrates the acceleration over time to produce a vertical velocity. The stimulation device further monitors minute ventilation. The device determines the patient's position and activity status from the acceleration data, velocity data, and minute ventilation data. Such data is used, for example, to detect whether the patient moves from a supine to an upright position, or to discern between a patient ascending upstairs or descending downstairs.

Exemplary Stimulation Device

The techniques described below are intended to be implemented in connection with any stimulation device that is configured or configurable to stimulate or shock a patient's heart.

Figure 1:
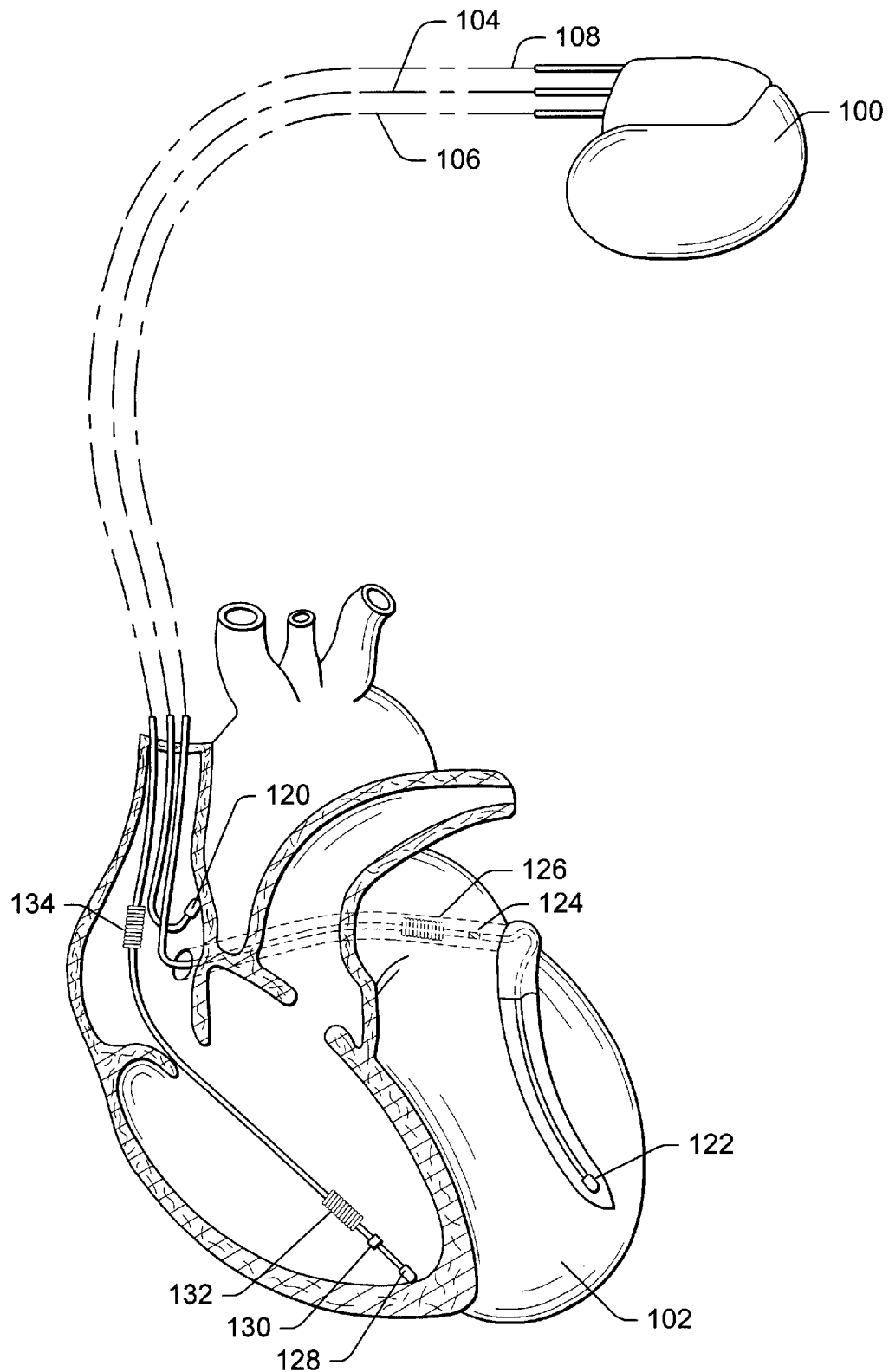
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126.

Stimulation device 100 is also shown in electrical communication with the s patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
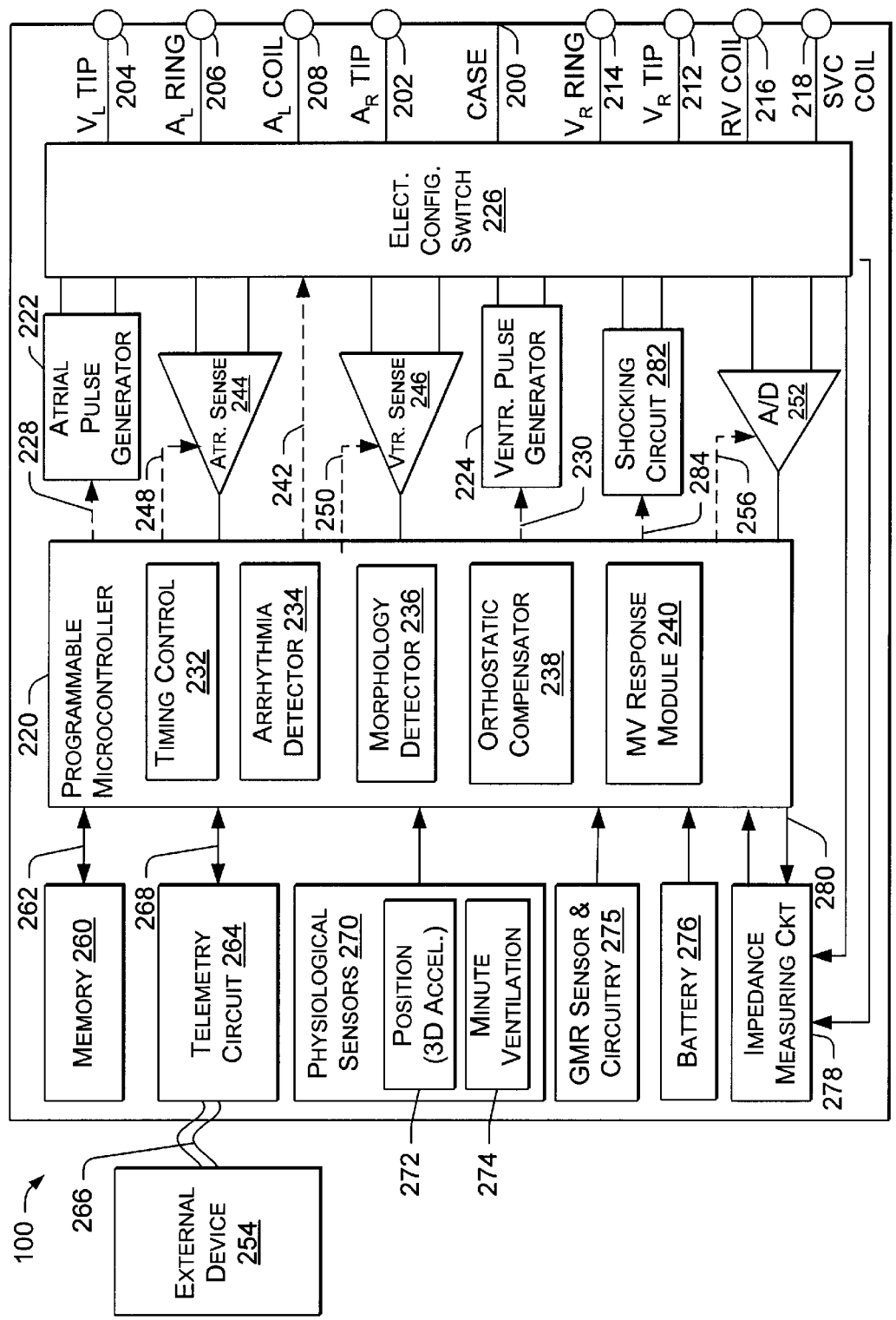
FIG. 2 is a functional block diagram of a multi-chamber implantable stimulation device illustrating basic elements that are configured to provide cardioversion, defibrillation, and pacing stimulation in four chambers of the heart. The implantable stimulation device is further configured to detect onset of orthostatic hypotension and apply therapy to reduce the effects of orthostatic hypotension.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, an orthostatic compensator 238, and a minute ventilation (MV) response module 240. These components can be utilized by the stimulation device 100 for determining desirable times to administer various therapies, including those to reduce the effects of orthostatic hypotension, as will become more apparent below. The components 234–240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state.

More specifically, the physiological sensors 270 include sensors for detecting movement and minute ventilation in the patient. Any sensor capable of sensing changes in movement or minute ventilation, either directly or indirectly, may be used. In particular, the physiological sensors 270 include a position sensor 272 mounted within the housing 200 of the stimulation device 100 to detect movement in the patient's position. The position sensor 272 may be implemented in many ways. In one particular implementation, the position sensor 272 is implemented as a three-dimensional (3D) accelerometer-based sensor that measures the acceleration on the sensor 120 resulting from movement. Body movement of the patient will result in a high amplitude signal from the accelerometer. For example, the accelerometer-based sensor provides a signal to the microcontroller 220 that can be processed to indicate that the patient is undergoing heightened physical exertion or is moving directionally upwards or downwards.

The physiological sensors 270 further include a minute ventilation (MV) sensor 274 to sense minute ventilation, which is defined as the total volume of air that moves in and out of a patient's lungs in a minute. The MV sensor 274 uses transthoracic impedance, which is a measure of impedance across the chest cavity. Lungs filled with air have higher impedance than empty lungs. Thus, upon inhalation, impedance increases; whereas upon exhalation, impedance decreases.

Signals generated by the position sensor 272 and MV sensor 274 are passed to the microcontroller 220 for analysis in determining whether to adjust the pacing rate, invoke the orthostatic compensator 238, and/or invoke the MV response module 240. The microcontroller 220 monitors the signals for indications of the patient's position and activity status, such as whether the patient is climbing upstairs or descending downstairs or whether the patient is sitting up after lying down.

More specifically, the microcontroller 220 receives a signal from the 3D accelerometer-based sensor 272 that may be processed to produce an acceleration component along a vertical axis (i.e., z-axis signal). The acceleration component can be used to determine whether there is an increased or decreased level of activity in the patient. The microcontroller 220 integrates that signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke the orthostatic compensator 238 to apply a prescribed pacing therapy, especially at the onset. If the patient is traversing downstairs, the device might decrease the pacing rate or perhaps invoke the MV response module 240 to control pacing therapy during the descent. The MV response module 240 determines a suitable pacing rate by, for example, measuring the transthoracic impedance from the MV sensor 274, computing the current MV, and comparing that with a long-term average of MV.

The microcontroller 220 can also monitor the sensor signals for any indication that the patient has moved from a supine position to an upright position. For example, the integrated velocity signal computed from the vertical acceleration component of the sensor data can be used to determine that the patient has just stood up from a chair or sat up in bed. A sudden change in the vertical signal, particularly following a prolonged period with little activity while the patient is sleeping or resting, confirms that a posture-changing event occurred. The microcontroller 220 uses this information as one potential condition for deciding whether to invoke the orthostatic compensator 238 to apply cardiac pacing therapy for treating orthostatic hypotension.

The stimulation device 100 may also be equipped with a GMR (giant magnetoresistance) sensor and circuitry 275 that detects the earth's magnetic fields. The GMR sensor and circuitry 275 may be used to ascertain absolute orientation coordinates based on the earth's magnetic fields. The device is thus able to discern a true vertical direction regardless of the patient's position (i.e., whether the patient is lying down or standing up). The three-axis orientation coordinates measured by the 3D accelerometer-based sensor 272 may then be taken relative to the absolute orientation coordinates from the GMR. For instance, as a person sits up, the axial coordinates of the 3D accelerometer-based sensor 272 might change by 90°, but the sensor signals may be calibrated as to the true vertical direction based on the output of the GMR sensor and circuitry 275.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium derivative battery chemistries.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (up to 0.5 Joules), moderate (0.5–10 Joules), or high energy (11 to 40 Joules), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Posture and Descending/Ascending Detection

Figure 3:
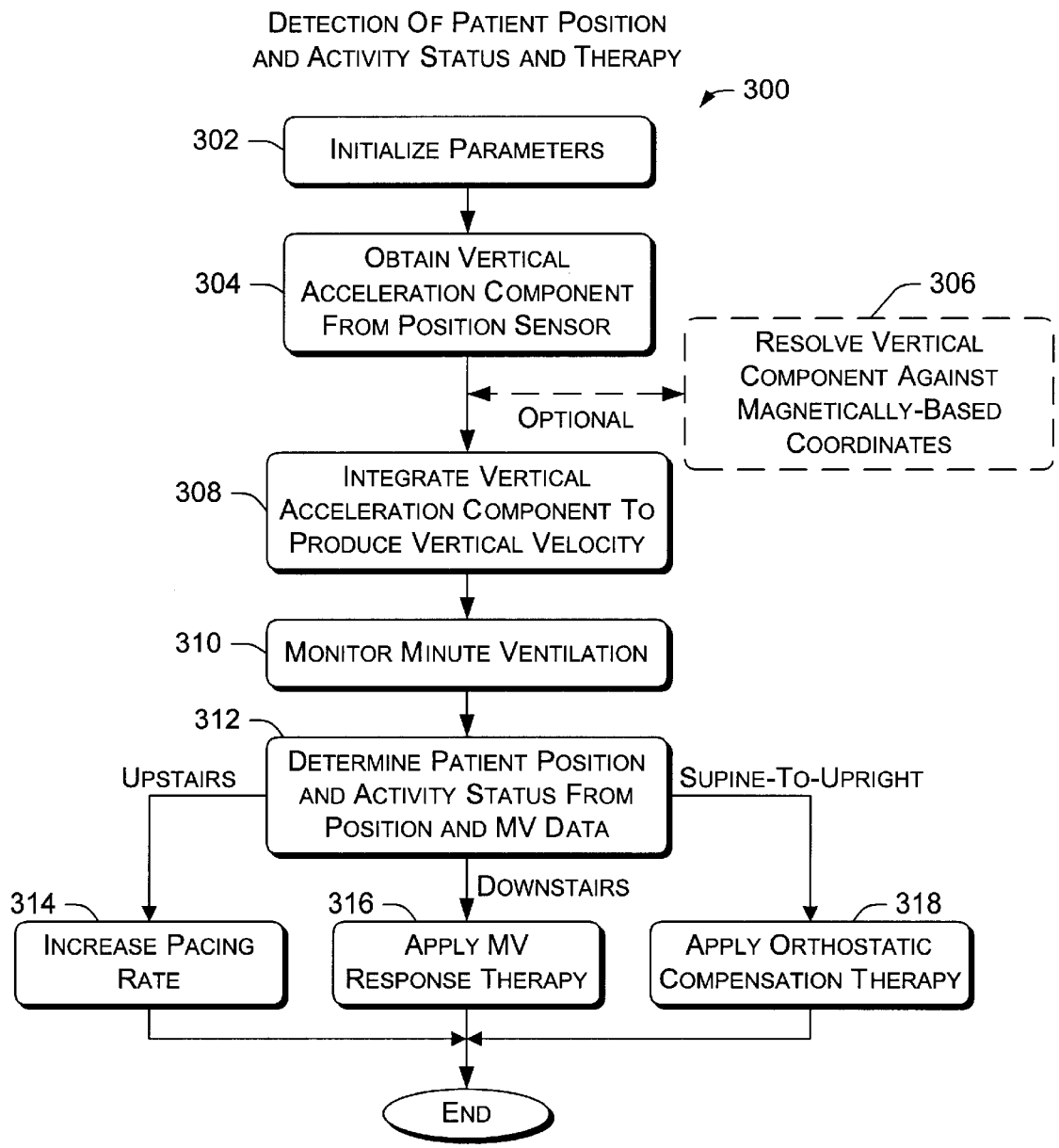
FIG. 3 is a flow diagram of a process to detect a patient's position and activity status and administer an appropriate pacing therapy.

FIG. 3 shows an exemplary process 300 for detecting a patient's position and activity status and for administering an appropriate pacing therapy based on that status. The method can be implemented in connection with any suitably configured stimulation device. One specific and non-limiting example of a stimulation device was described above with respect to FIGS. 1 and 2.

In this flow diagram, various algorithmic acts are summarized in individual "blocks". Such blocks describe specific actions or decisions that are made or carried out as the process proceeds. Where a microcontroller (or equivalent) is employed, the flow charts presented herein provide a basis for a "control program" or software/firmware that may be used by such a microcontroller (or equivalent) to effectuate the desired control of the stimulation device. As such, the process 300 is implemented as machine-readable instructions stored in memory that, when executed by a processor, perform the various acts illustrated as blocks.

Those skilled in the art may readily write such a control program based on the flow charts and other descriptions presented herein. It is to be understood and appreciated that the inventive subject matter described herein includes not only stimulation devices when programmed to perform the steps described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

At block 302, the parameters used in monitoring a patient's position and activity are initialized. Such parameters include position information, such as data from the three directional axes of the position sensor 272, or time-based position data captured over a period of time, or any other position data indicative of changes in a patient's position. Such data may also include benchmark output by the GMR sensor 275. Additionally, the initialization operation may involve computing a long-term average of minute ventilation for use by the Mv response module 240, as well as a threshold level that would indicate a significant increase in minute ventilation that is indicative of increased physical exertion.

At block 304, the device 100 monitors the position data being sensed by position sensor 272. More specifically, the 3D accelerometer-based sensor outputs signals that, when processed, are indicative of acceleration along three orthogonal coordinates. The microcontroller 220 tracks the acceleration component along a vertical axis (i.e., z-axis). Optionally, the vertical acceleration signal can be resolved against the vertical axis as determined by the GMR sensor and circuitry 275 (block 306). The vertical acceleration component can be used as one parameter in detecting a patient's position and activity status, such as when the patient is moving vertically (e.g., climbing upstairs or descending downstairs) or when the patient changes from a supine position to an upright position.

At block 308, the microcontroller 220 integrates the vertical acceleration component over time to produce a vertical velocity. The integration can either be performed using a hardware integrator, or the microcontroller can incorporate software, which will mathematically integrate over time the acceleration signal provided by the position sensor 272. The vertical velocity is another parameter that can help discern a patient's activity status by suggesting, for example, whether the patient is going upstairs or downstairs.

At block 310, the device monitors the minute ventilation data sensed by MV sensor 274. The MV data provides yet another possible parameter can be used for determining a patient's activity status.

At block 312, the device determines the patient's position and activity status from the acceleration data, velocity data, and MV data. For example, activity in the vertical acceleration component following little activity might indicate that the patient has moved from a supine to an upright position. As another example, the combination of the acceleration data, vertical velocity, and the MV data can be used to discern between a patient ascending upstairs or descending downstairs.

Figure 4:
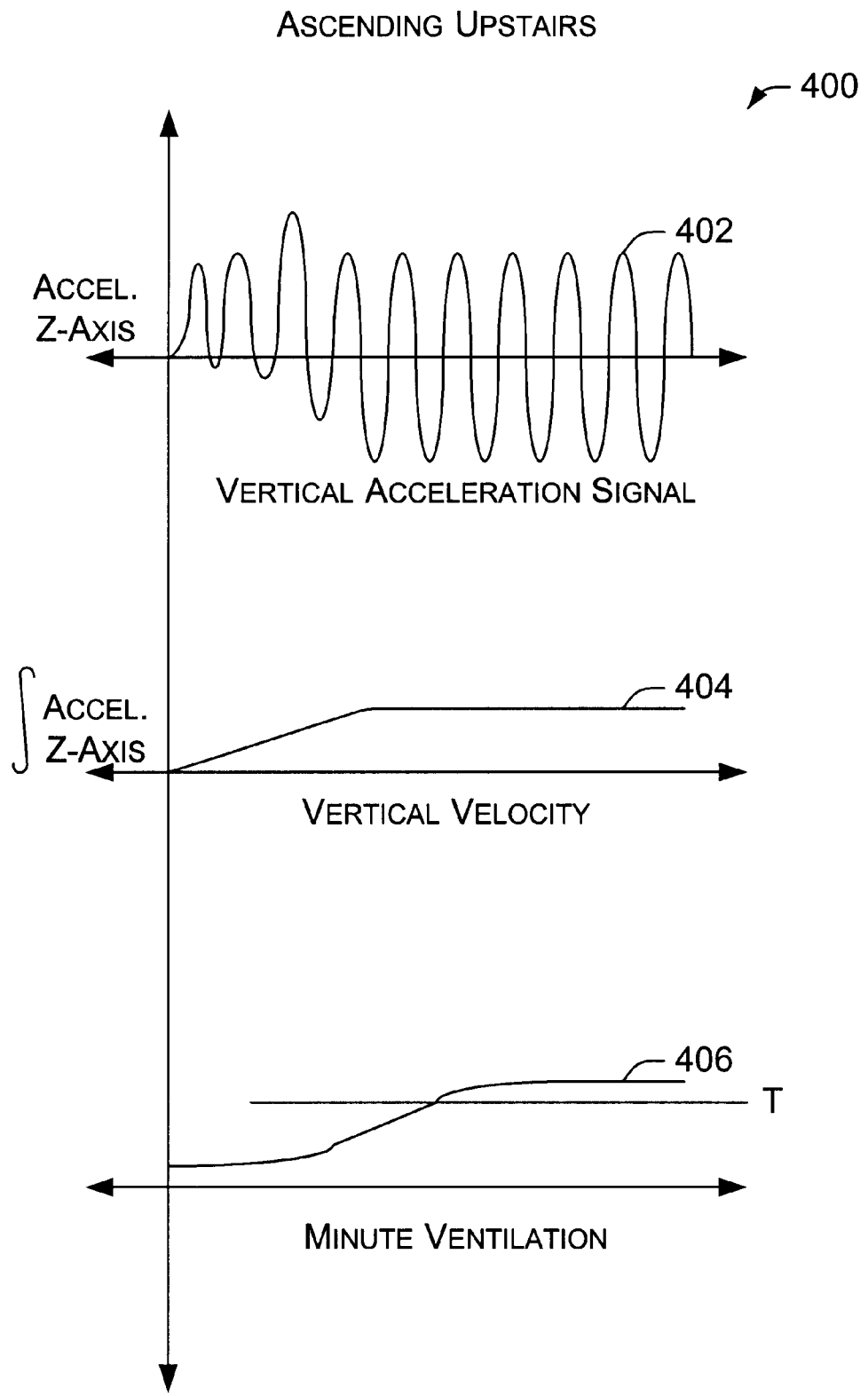
FIG. 4 shows graphs of acceleration data, velocity data, and minute ventilation data that are suggestive of a patient climbing stairs.

FIG. 4 shows an example of a set of data 400 that is indicative of a patient moving vertically upwards (e.g., walking or running upstairs, scaling up a hill or mountain, etc.). The top graph illustrates an acceleration signal 402 taken along the vertical axis (i.e., the z-axis signal). The up-and-down nature of the accelerometer signal represents the vertical movement of the patient walking upstairs. The middle graph shows the vertical velocity 404 that is integrated from the acceleration signal 402. Notice that the velocity signal is positive and increases as the patient begins up the stairs, and then smoothes to a constant velocity as the patient hits a normal stride. The bottom graph shows the MV data 406 taken during this climbing activity. Initially, the minute ventilation is low. But, as the user climbs the stairs and requires more oxygen to fuel the muscle activity, the MV amplitude begins to increase to a heightened level as the user is breathing harder. If the MV amplitude crosses a threshold T, the MV amplitude confirms that the patient is indeed climbing the stairs. In this manner, the activity in the vertical acceleration signal, coupled with a positive vertical velocity and an MV increase, is suggestive of a user ascending stairs.

With reference to FIG. 3, if a determination is made that the patient is ascending stairs (or other vertical object), the microcontroller 220 increases the pacing rate (block 314). The microcontroller 220 may further decide to invoke the orthostatic compensator 238 to apply pacing therapy to avoid orthostatic hypotension that maybe brought on as a result of climbing the stairs.

Figure 5:
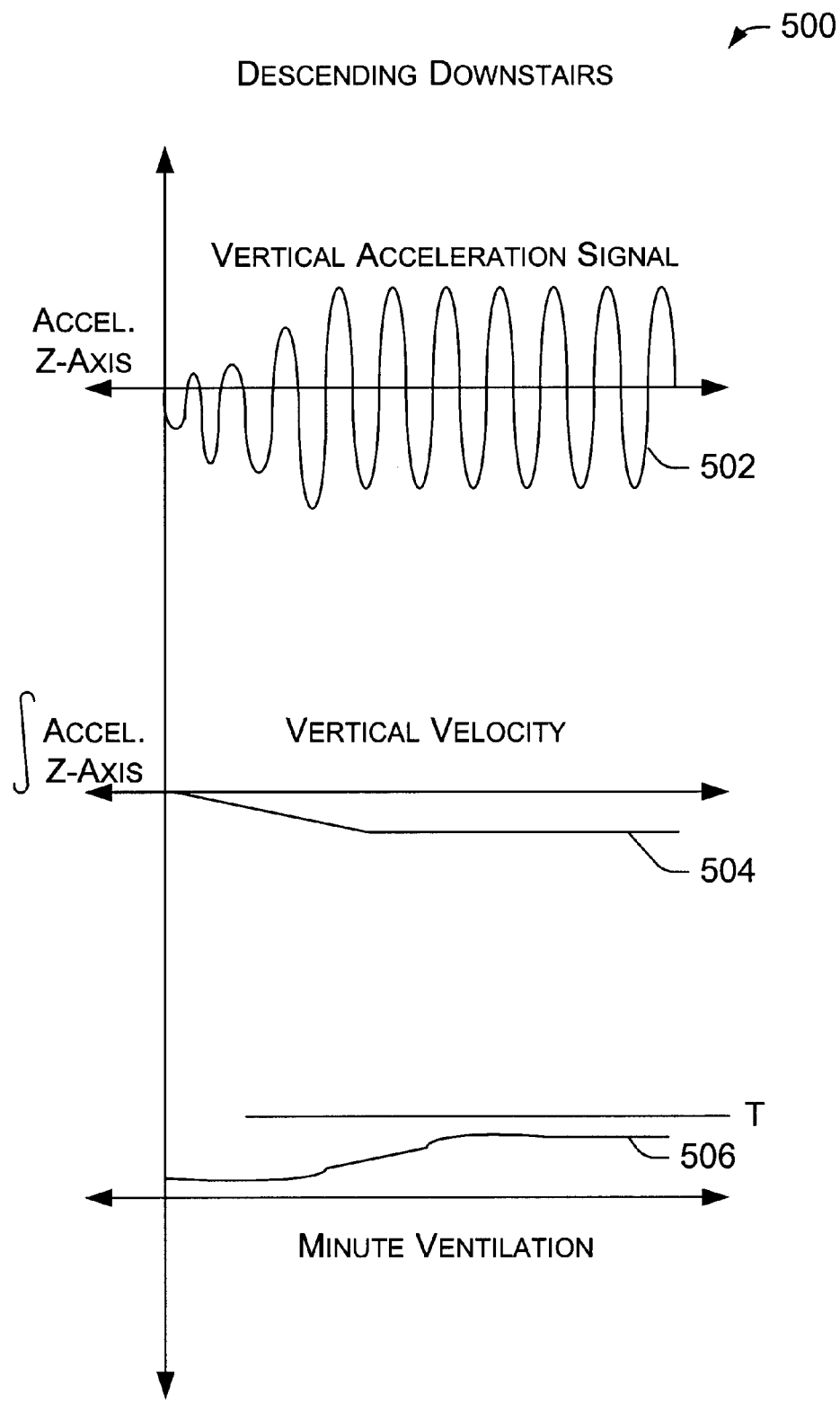
FIG. 5 shows graphs of acceleration data, velocity data, and minute ventilation data that are suggestive of a patient descending downstairs.

FIG. 5 shows an example set of data 500 that is indicative of a patient descending vertically downward (e.g., downstairs). As before, the top graph illustrates an acceleration signal 502 taken along the vertical axis (i.e., the z-axis signal) and the middle graph shows the vertical velocity 504 that is integrated from the acceleration signal 502. In this case, the velocity signal is negative and the amplitude increases slightly as the patient moves down the stairs before smoothing to a constant velocity as the patient reaches normal stride. The bottom graph shows the MV data taken during this climbing activity. Initially, the minute ventilation is low. As the user continues downstairs, the MV may increase slightly, but not nearly as much as the case of climbing stairs. Hence, the MV amplitude never reaches the threshold T. In this manner, the activity in the vertical acceleration signal, coupled with a negative vertical velocity and a comparatively minor increase in the MV value, is suggestive of a user descending stairs.

With reference again to FIG. 3, upon a determination that the patient is moving downstairs (or other vertical object), the microcontroller 220 may opt to decrease the pacing rate or, perhaps, rely more on the minute ventilation response module 240 to set an appropriate pacing rate (block 316).

Figure 6:
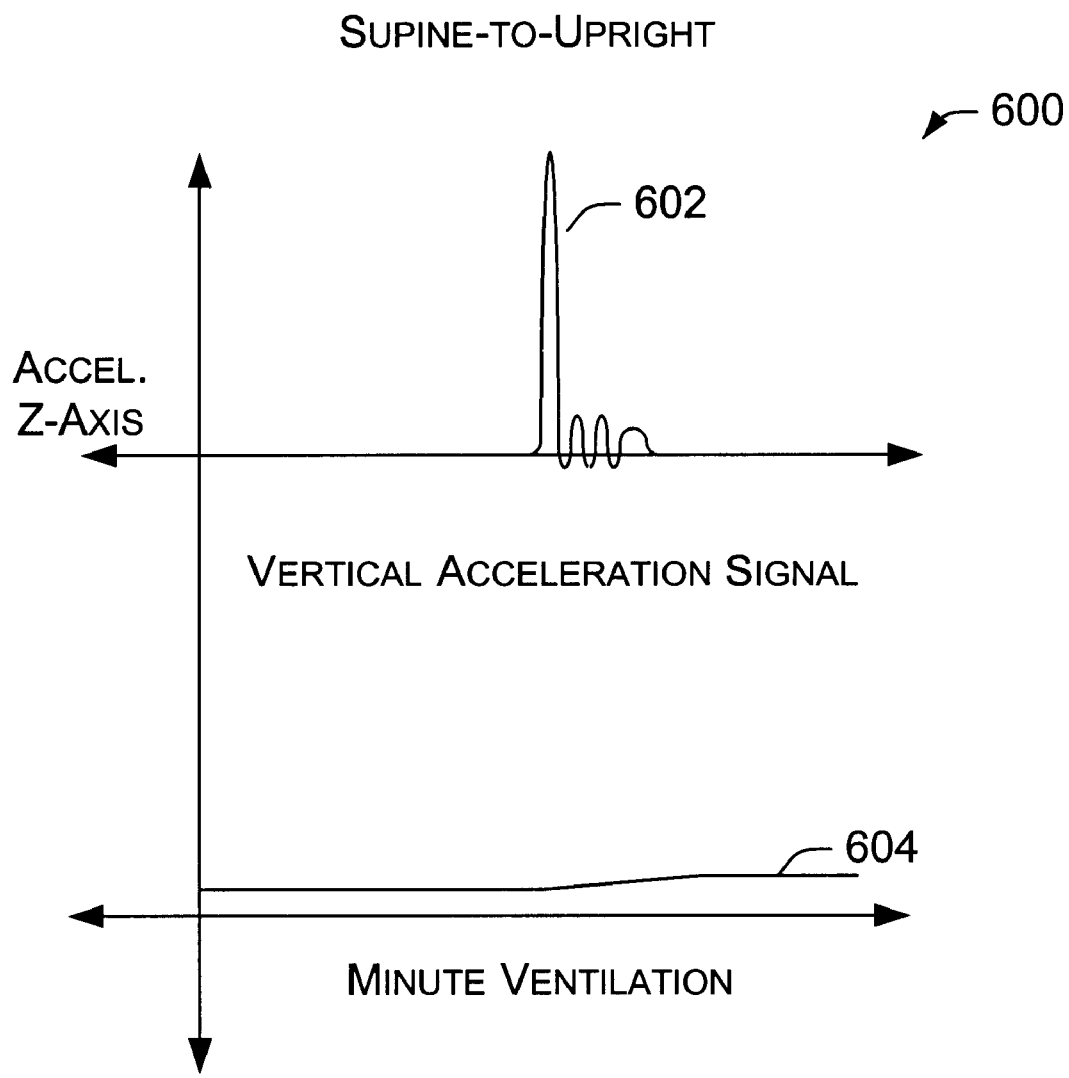
FIG. 6 shows graphs of acceleration data and minute ventilation data that are suggestive of a patient moving from a supine to an upright position.

The microcontroller 220 may further determine that the patient is moving from a supine to an upright position, based on the acceleration data. FIG. 6 shows an exemplary set of data 600 representative of a patient sitting or standing up from a reclined position. A vertical acceleration signal 602 is relatively quiet until the patient sits or stands up. This movement causes a sudden spike in the vertical acceleration. There may also be a slight increase in the minute ventilation as the patient begins to breath heavier in a non-rest state.

To prevent or reduce the effects of any orthostatic hypotension resulting from this movement, the microcontroller 220 may invoke the orthostatic compensator to apply a suitable pacing therapy (block 318 in FIG. 3).

Figure 7:
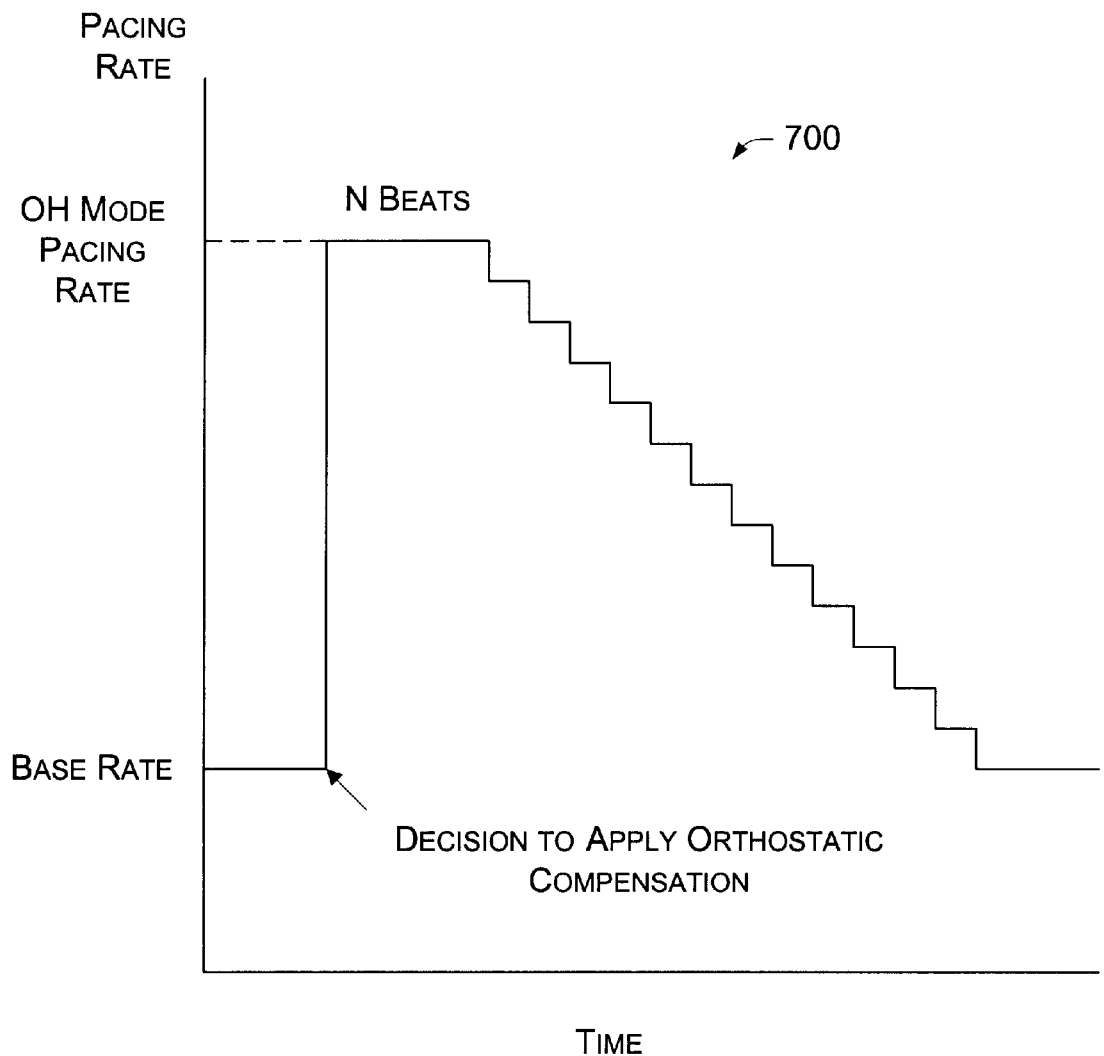
FIG. 7 is a graphical illustration of a pacing therapy effective for treating orthostatic hypotension.

FIG. 7 shows an exemplary pacing therapy 700 that is applied by the orthostatic compensator 238. Initially, the pacing rate is at a base rate of, say, 50–70 pulses per minute (ppm). When the patient moves to the upright position, the pacing rate is adjusted from the base rate to an upper pacing rate programmed into an orthostatic hypotension (OH) mode. As an example, the OH mode pacing rate may be approximately 100 ppm, although these rates are programmable for individual patients. This increased rate is maintained for a programmable number of beats or predetermined time period. The increased pacing rate causes the heart to beat faster, pumping more blood into the system and hence, increasing blood pressure.

After a predetermined period or number of beats, the device 100 systematically begins decreasing the pacing rate toward a reduced rate. The pacing rate reduction is performed gradually over a period of time, as indicated by the step-wise curve of therapy 700 in FIG. 7.

It is noted that the above described processes and systems may be used to treat other conditions that are similarly impacted by changes in the patient's posture. For instance, the processes and systems may be used to treat vasovagal syncope.

The vertical acceleration signal, or velocity integrated therefrom, may be used in other ways as well. For instance, in a multi-sensor system, various sensors are often assigned weights to adjust how much influence a given sensor contributes to pacing decisions. The vertical acceleration signal, or velocity, may be used to adjust the weights assigned to the sensors. As an example, suppose the patient is carrying groceries into the house from the car. The positional sensor shows normal amounts of acceleration, while the MV sensor indicates a heavier breathing rate cased by the exertion to carry the weight of the groceries. In this situation, the device may decide to increase the weighting on data from the MV sensor and decrease the weighting on acceleration data from the position sensor to prescribe a more accurate pacing remedy for the patient's activity.

CONCLUSION

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method for operating an implantable stimulation device, comprising:

sensing data using a position sensor;

sensing an orientation using an external field sensor; and resolving the data according to the vertical orientation to adjust orientation of the position sensor.

2. The method of claim 1, wherein the sensing an orientation comprises sensing a magnetic field using a magnetic field sensor.

3. The method of claim 1, further comprising deriving, from the data, a vertical acceleration parameter indicative of a patient's acceleration in a vertical direction.

4. The method of claim 3, further comprising determining, based on the vertical acceleration parameter, whether the patient moves from a supine position to an upright position.

5. The method of claim 4, further comprising applying a prescribed pacing therapy based on the vertical acceleration parameter.

6. The method of claim 4, further comprising invoking an orthostatic compensator to apply a prescribed pacing therapy.

7. The method of claim 3, further comprising computing a vertical velocity parameter from the vertical acceleration parameter and determining, based on the vertical velocity parameter, whether the patient is walking upstairs or downstairs.

8. The method of claim 7, further comprising:

increasing pacing rate if the patient is walking upstairs; and decreasing pacing if the patient is walking downstairs.

9. The method of claim 7, further comprising:

invoking an orthostatic compensator to apply a prescribed pacing therapy if the patient is walking upstairs; and invoking a MV response module to control pacing therapy.

10. The method of claim 7, further comprising determining, based on the vertical acceleration parameter, whether the patient moves from a supine position to an upright position.

11. The method of claim 10, further comprising:

increasing pacing rate if the patient is walking upstairs;

applying a MV response therapy if the patient is walking downstairs; and applying an orthostatic compensation therapy if the patient moves from the supine position to the upright position.

12. One or more computer-readable media having computer-readable instructions thereon which, when executed by a programmable stimulation device, cause the stimulation device to execute the method of claim 1.

13. A method for operating an implantable stimulation device, comprising:

sensing an external magnetic field to produce orientation data; and determining a patient's positional status based at least in part on the orientation data.

14. The method of claim 13, further comprising ascertaining whether a user moves from a supine position to an upright position based on the orientation data.

15. The method of claim 13, wherein the external magnetic field is the earth's magnetic field.

16. The method of claim 15, wherein the sensing a magnetic field further comprises:

discerning a true vertical direction by ascertaining orientation coordinates based on the earth's magnetic field.

17. One or more computer-readable media having computer-readable instructions thereon which, when executed by a programmable stimulation device, cause the stimulation device to execute the method of claim 13.

18. A cardiac stimulation device comprising:

a position sensor to sense a patient's position relative to at least one axis;

a magnetic field sensor to sense a magnetic field and produce data indicative of directional orientation;

a processor operably coupled to the position sensor and the magnetic field sensor, the processor being configured to use the directional orientation of the magnetic field sensor to correct orientation of the axis of the position sensor; and a pacing generator configured to administer cardiac pacing therapy as directed by the processor.

19. The device of claim 18, wherein the at least one axis is a vertical axis.

20. The device of claim 19, wherein the processor computes a vertical acceleration parameter from the data, and wherein the vertical acceleration parameter is indicative of a patient's acceleration in a vertical direction.

21. The device of claim 20, wherein the processor applies the vertical acceleration parameter to determine whether the patient moves from a supine position to an upright position.

22. The device of claim 21, wherein the processor computes a vertical velocity parameter from the vertical acceleration parameter, and wherein the processor applies the vertical velocity parameter to determine whether the patient is walking upstairs or downstairs.

23. The device of claim 22, wherein the cardiac pacing therapy comprises:

increasing pacing rate if the patient is walking upstairs;

applying a MV response therapy if the patient is walking downstairs; and applying an orthostatic compensation therapy if the patient moves from the supine position to the upright position.

* * * * *